US00PP10514P

United States Patent [19]

Lemon

[11] Patent Number: Plant 10,514

[45] Date of Patent: Jul. 21, 1998

[54] VARIETY OF GERANIUM PLANT NAMED 'GLOBAL ROSE'

[75] Inventor: David Lemon, Lompoc, Calif.

[73] Assignee: John Bodger & Sons Company, S. El Monte, Calif.

[21] Appl. No.: 724,700

[22] Filed: Oct. 1, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 7,358 10/1990 Guillou et al. ..... Plt./87.12

P.P. 7,720 11/1991 Guillou et al. ..... Plt./87.12

*Primary Examiner*—Howard J. Locker

*Attorney, Agent, or Firm*—Fulwider Patton Lee & Utecht, LLP

[57] ABSTRACT

The cultivar is characterized by the lavender-rose color of the bloom over medium green zoned foliage. Its quick rooting time and continuous flowering provides for superb cuttings and for quick recovery of the bloom following wet weather conditions. The blooms are slow to shatter, and an abundant amount of cuttings may be obtained from a single plant.

1 Drawing Sheet

BACKGROUND OF THE NEW PLANT

The present invention comprises a new and distinct cultivar of *Pelargoniun×peltatum* known by the varietal name Global Rose (Oglevee No. 3040, Bodger No. 2GM 214-1). The new variety was discovered in a selective breeding program by David Lemon at Bodger Seeds, Ltd., Lompoc, Calif. The new variety is a selection from the crossing of Nicole (U.S. Plant Pat. No. 7,358) with Salmon Queen (Bodger No. 1 GM 225 unpatented) both of which patents are characterized by a candy pink flower and medium green foliage while the claimed cultivar has a lavender-rose flower with medium green zoned foliage.

The new cultivar was first asexually reproduced by cuttings at Oglevee Ltd., Connellsville, Pa. and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa. using full light, 60° Fahrenheit night temperature, 68° Fahrenheit day temperature, 72° Fahrenheit vent temperature and grown in a soilless media of constant fertilizer 200–250 parts per million of nitrogen and potassium has a response time of six weeks from the rooted cutting to a flowering plant in a 10.0 cm pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted on approximately Feb. 1, 1996 and flowering on approximately Mar. 4, 1996 under full light and greenhouse, and colorings were taken indoors under 200–220 foot candles of fluorescent cool white light using the R.H.S. Colour Chart of The Royal Horticultural Society of London.

THE PLANT

Classification:

*Botanical.*—*Pelargonium×peltatum.*

*Commercial.*—*Ivy Geranium Global Rose.*

Form: Cascading mound.

*Height.*—200–23.0 cm from media surface.

*Growth.*—Cascading side growth; free branching.

*Strength.*—Holds upright mound shape while allowing outer branches to cascade.

Foliage: Stalked leaf attachment.

Leaves:

*Size.*—7.0–8.5 cm.

*Shape.*—Reniform; cordate base.

*Margin.*—Pedately lobed.

*Texture.*—Slightly reflective; leathery; slightly pubescent.

*Color.*—Top: Green group 137C. Bottom: Yellow green group 146B. Zone: Greyed- purple group 187A.

*Ribs and veins.*—Palmate venation: Color: Yellow green group 146C.

Petioles:

*Length.*—5.5–7.0 cm.

*Color.*—Yellow-green group 146C.

Stem:

*Color.*—Yellow green group 146C.

*Internodes.*—2.5–4.0 cm in length.

THE BUD (UMBEL)

Shape: Elliptical cluster

Size: 2.5–3.5 cm—no color showing

INFLORESCENCE

Blooming habit: Free and early; continuous.

Borne: Florets on pedicel; pedicel on peduncle.

Closed florets:

*Bud size.*—1.0–1.3 cm in length; 5 mm across.

Size:

*Fully open bloom.*—12.0–13.0 cm.

Open florets:

*Form.*—Flat to slightly cupped, semi-double.

*Color.*—Top: Red-purple group 68A. Bottom: Red-purple group 68B. Eye: Red-purple group 71B the appearance of the darker eye is not a prominent characteristic of the plant.

*Petals.*—11-13 in number; about 5 florets per inflorescence.

*Size.*—5.5–6.0 cm.

*Texture and appearance.*—Satiny; appearance from a distance is lavender-rose flower above medium green zoned foliage.

Petaloids:

*Quantity.*—9–11.

*Shape.*—Elongated, twisted, some with pollen attached (the structure may not change completely to a full petaloid form and may retain some anther characteristics).

*Color.*—Top: Red-purple group 68A. Bottom: Red-purple group 68B.

Pedicel:

*Length.*—2.0–3.5 cm.

*Color.*—Yellow — green group 146B.

Peduncle:

*Length.*—15.0–18.5 cm.

*Color.*—Yellow green group 146 B.

Persistence:

*Disease resistance.*—Not known.

*Lasting quality.*—Slow to shatter; these plants have been found to have very good garden performance.

REPRODUCTIVE ORGANS

Stamens:

*Anthers.*—Length: 2 mm.

*Filaments.*—Length: 0.9–1.1 cm. Color: White.

*Pollen.*—Golden brown.

Pistils:

*Number.*—One; 5 parted.

*Length.*—0.6–1.1 cm.

*Stigma.*—Color: Red purple.

*Style.*—Length: 2–4 mm.

Ovaries: Color: Pale green, pubescent, superior. Length: 4–5 mm.

Fruit: None.

GENERAL CHARACTERISTICS

Global Rose is similar in color to the current market variety Monique (U.S. Plant Pat. No. 7,720 which presents a more lavender color as compared to the claimed cultivar which is a rose-pink flower including the sporadic appearance of a darker eye. It has a very distinct zone, controlled mound and cascading habit, is less sensitive to soluble salts, and has a relatively faster rooting speed. Cutting production and finishing are exceptional.

I claim:

1. A new and distinct variety of Geranium plant, substantially as shown and described.

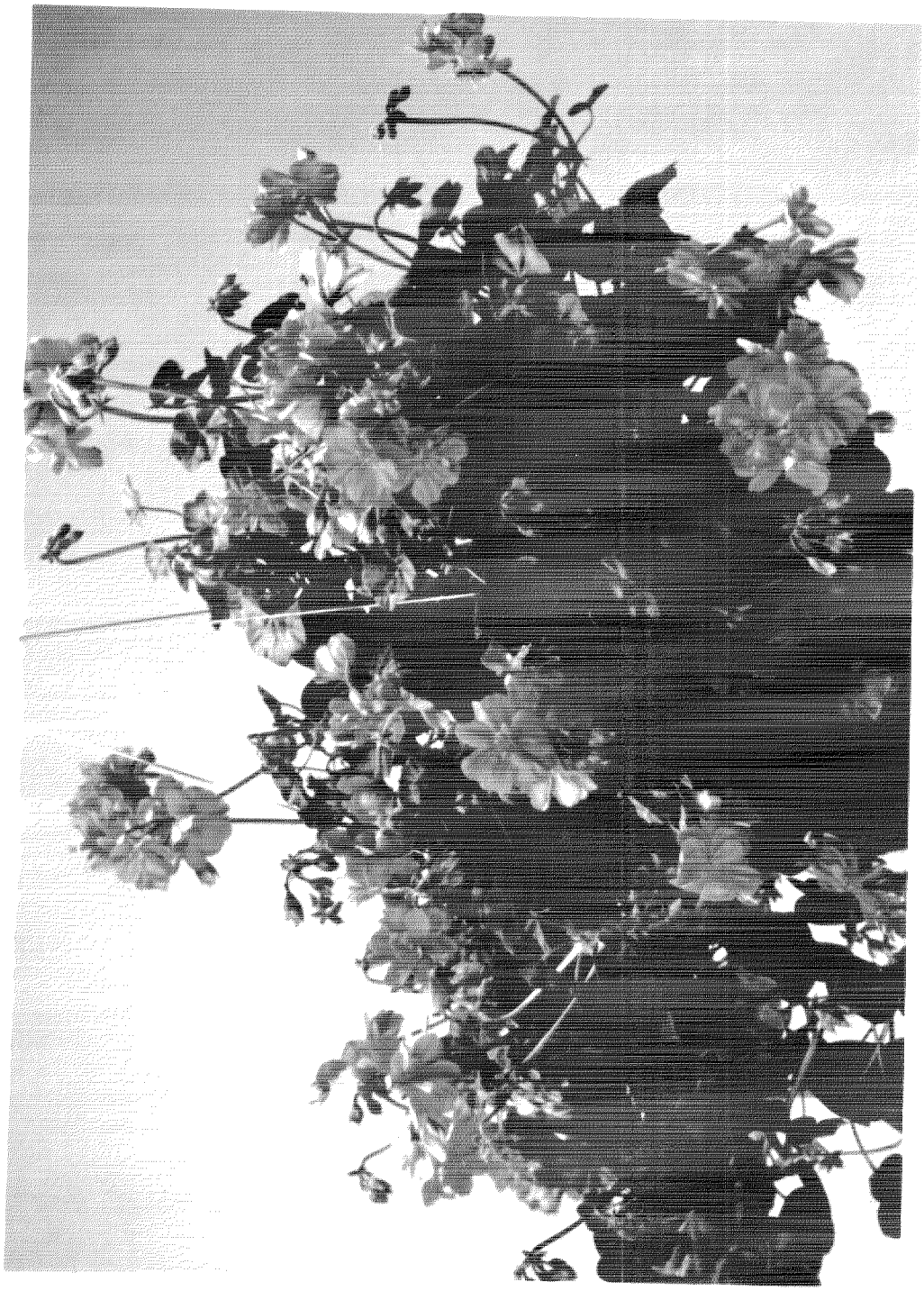

* * * * *